(12) United States Patent
Kogan (10) Patent No.: US 7,516,031 B2
(45) Date of Patent: Apr. 7, 2009

(54) APPARATUS AND METHOD FOR CORRECTING FOR ABERRATIONS

(75) Inventor: Vladimir Kogan, Enschede (NL)

(73) Assignee: PANalytical B.V., Almelo (NL)

( * ) Notice: Subject to any disclaimer, the term of this patent is extended or adjusted under 35 U.S.C. 154(b) by 206 days.

(21) Appl. No.: 11/370,238

(22) Filed: Mar. 7, 2006

(65) Prior Publication Data

US 2006/0206278 A1 Sep. 14, 2006

(30) Foreign Application Priority Data

Mar. 10, 2005 (EP) .................................. 05251451

(51) Int. Cl.
*G01R 23/16* (2006.01)
(52) U.S. Cl. .............................. 702/77; 702/27; 702/28
(58) Field of Classification Search .................... 702/77, 702/27, 28
See application file for complete search history.

(56) References Cited

U.S. PATENT DOCUMENTS

| 5,430,786 | A | * | 7/1995 | Komatsu et al. | .............. 378/45 |
| 5,748,509 | A | | 5/1998 | Fewster | ..................... 364/578 |

OTHER PUBLICATIONS

Marinovic et al., "A Comparison between the Warren-Averbach Method and Alternate Methods for X-Ray Diffraction Microstructure Analysis of Polycrystalline Specimens", Materials Research, vol. 4, No. 2, 2001, pp. 71-76.

Boulle A. et al., "A high-resolution X-ray diffractometer for the study of imperfect materials", Journal of Applied Crystallography Munksgaard International Booksellers & Publishers, Denmark, vol. 35, Oct. 2002, pp. 606-614.

Keating, D.T., "Elimination of the alpha!1 alpha!2 doublet in x-ray patterns" Review of Scientific Instruments USA, vol. 30, No. 8, Aug. 1959, pp. 725-727.

Louer D. et al., "Peak shape and resolution in conventional diffractometry with monochromatic X-rays", Journal of Applied Crystallography, Denmark, vol . 21, Oct. 1, 1988, pp. 430-437.

Godwod K. et al., "Mathematical analysis of the high-resolution reciprocal space map", Journal of Physics D (Applied Physics) IOP Publishing, UK, vol. 36, No. 10A, May 21, 2003, pp. A148-A152.

Masson O. et al., "Modelling of line profile asymmetry caused by axial divergence in power diffraction", Journal of Applied Crystallography Munksgaard International Booksellers & Publishers, Denmark, vol. 34, Aug. 2001, pp. 436-441.

Ida T. et al., "Deconvolution of instrumental aberrations for synchrotron powder X-ray diffractometry", Journal of Applied Crystallography Munksgaard International Booksellers & Publishers, Denmark, vol. 36, Apr. 2003, pp. 181-187.

(Continued)

*Primary Examiner*—Bryan Bui
*Assistant Examiner*—Stephen J Cherry
(74) *Attorney, Agent, or Firm*—Bromberg & Sunstein LLP (57) ABSTRACT

A method of correcting for aberrations in scattering data is described which does not require prior knowledge about the sample microstructure properties or calculations based on the modelling of peak locations. In an example, X-ray scattering apparatus integrates a correction device arranged to automatically calculate and output aberration corrected output X-ray pattern using the aberration Fourier presentation $F_{inst}(H,2\theta)$ dependent from the scattering angle $2\theta$ and the Fourier transform of the measured X-ray scattering pattern $F_{exp}(H)$.

23 Claims, 5 Drawing Sheets

OTHER PUBLICATIONS

Stokes A.R., "A numerical Fourier-analysis method for the correction of widths and shapes of lines on X-ray powder photographs", Proceedings of the Physical Society, UK, vol. 61, Oct. 1948, pp. 382-391.

International Search Report dated Aug. 25, 2005.

Ladell, J. et al., "*Cu $Ka_2$ Elimination Algorithm*," J. Appl. Cryst. 8, 499-506 (1975).

Cheary et al. "A Fundamental Parameters Approach to X-Ray Line-Profile Fitting," *J. Appl. Crys,.* 25, 109-121 (1992).

Ida "New Approach to Eliminate the Instrumental Aberrations From Powder X-Ray Diffraction Data Based on a Fourier Method," *The Rigaku Journal*, vol. 20, No. 2, 12-20 (2003).

Kogan et al. "X-Ray Powder Diffraction Line Profiles by Fourier Synthesis," *J. Appl. Cryst,.* 25, 16-25 (1992).

* cited by examiner

APPARATUS AND METHOD FOR CORRECTING FOR ABERRATIONS

CROSS REFERENCE TO RELATED APPLICATIONS

This application claims priority from European Patent Application Serial No. 05251451.0, filed on Mar. 10, 2005, which is hereby incorporated by reference, in its entirety.

TECHNICAL FIELD

The invention relates to a method of correcting for aberrations, particularly but not exclusively in the field of x-ray diffraction, and to an apparatus for implementing the method as well as a computer program product arranged to cause the method to be implemented.

BACKGROUND ART

X-ray scattering measurements of polycrystalline or amorphous samples may be achieved by transmitting X-rays from a source to the sample and detecting the diffracted, scattered X-rays. The measured X-ray scattering pattern from the polycrystalline or amorphous substance normally consists of the superposition of overlapping multiple peaks, or components. For crystalline substances the true, so-called angular Bragg position of the peak is a function of crystallographic unit cell. Individual components are subjected to influence of instrumental and spectral aberrations, deforming and shifting the component from the original (Bragg) position. The aberrations are generally different for different F components.

Analysis of patterns with strongly overlapping components deformed by the aberrations may be complicated or even impossible to perform correctly.

A further problem is that the comparison of data measured with different optics on different systems or even using the same system at different times can be difficult due to the difference in instrumental aberrations. This makes it difficult to compare data taken at different times or on different equipment.

In general, therefore, the dependence of measured data on aberrations reduces accuracy and reliability of analytical results.

One example is the measurement of samples with peaks at low angles, which is typical of measurements carried out on pharmacological or nano-scale materials. As the result of the influence of instrumental aberrations, these peaks are strongly deformed and shifted from their theoretical Bragg positions. The pharmaceutical substances often exhibit polymorphism, and as a result that the real Bragg positions of the peaks are slightly different for different polymorphic phases. The effect of instrumental aberrations creates serious obstacles for undertaking analytical tasks such as indexing the crystallographic unit cell, phase identification by searching and matching in the reference patterns or discriminating between polymorphs.

Correction for instrumental aberrations is therefore required to obtain physically consistent information from different components in the pattern.

There are a few different approaches to use the information on instrumental aberrations for the correction analysis.

One approach is based on the introduction of a model to simulate superposition of separate peaks determined by a crystalline unit cell model. Profiles of separate peaks are presented empirically as for example in the so-called "Rietveld" method.

This approach assumes that knowledge of crystal structure, the structure of the unit crystalline cell, and/or the atomic structure is available to obtain the model of the scattering pattern. The model than may be compared with the measured pattern and the best fit is obtained by varying parameters of the model. There are other methods based on the peak model for example the "LeBail" method, where the peak positions are dependent on the unit cell but the peak shapes and weights are independent.

The non-empirical method to calculate the model of the peaks uses superposition from "first principles" by mathematical simulation of the instrument as set out in V. A. Kogan and M. Kupryanov, J. Appl. Cryst (1992), 25, 16-25 "X-Ray Diffraction Line Profiles by Fourier Synthesis" which describes a way in which line profiles can be calculated in Fourier space.

An alternative approach devoted to the non-empirical simulation of peak shapes in real space was described by R. W. Cheary and A. Coelho, J. Appl. Cryst (1992), 25, 109-121. "A Fundamental Parameters Approach to X-ray Line-Profile Fitting".

All these methods generally deal with a model of the diffraction peaks. While being powerful analytical tools, these approaches are not always convenient in the sense of the required input to the model.

Such calculations may be complicated and require a lot of operator input to obtain analytical result. For new materials with low symmetry, the complexity of the measured pattern may create obstacles for fast analysis or comparison.

There is a need therefore for a method to correct for aberrations without modelling the sample or the superposition of peaks, dealing with the pattern as a single continuum.

There are methods known in the art devoted to removing of Cu Kα2 and other spectral components of known shape. These methods generally based on identification of doublet or multiplet areas in the pattern and applying deconvolution in direct or Fourier space. These are also model based methods.

T. Ida and H. Toraya, J. Appl. Cryst, 35, 58-68 "Deconvolution of the instrumental functions in powder X-Ray diffractometry" and T. Ida, Rigaku Journal Volume 20, N2, December 2003 describe what appears to be a model independent approach for aberration correction. The authors suggest that they can correct the instrumental aberrations in the complete pattern. They use "rescaling" where for deconvolution of any instrumental function they are trying to find the scale transformation for 2θ angle such that this instrumental function would become constant. This approach does not require detailed knowledge of the crystal structure.

Unfortunately this approach is not general. It is of use to correct simple instrumental functions allowing correct rescaling to get the aberration constant.

Even though the method requires sophisticated analytical calculations and different scale conversions for the instrumental function applied, it is hardly applicable to anything other than very simple instrumental functions, and is accordingly unsuitable for most practically important functions of axial divergence, for correcting of any kinds of interacting functions such as functions of equatorial divergence interacting with sample transparency function for the cylindrical samples, etc.

It might be thought that an alternative useful way of reducing the aberrations would be to use appropriate optics. However, this would not be useful because it would imply the restriction of beam trajectories and therefore increase measurement time and decrease measurement quality.

SUMMARY OF INVENTION

According to the invention there is provided a method for correcting a measured scattering pattern containing multiple significantly distant components and/or peaks for the effects of aberration influencing the component and/or peak shapes and/or positions including:

i) inputting a measured pattern $f(2\theta)$ as a function of a parameter $2\theta$ representing the scattering angle, and calculating the representation of the measured pattern $f(2\theta)$ in a space for applying such corrections;

ii) obtaining a representation of an aberration function including a description of instrumental aberrations $F_{inst}$ depending on the parameter $2\theta$ in the same space; and iii) performing deconvolution of the calculated representation of $f(2\theta)$ to create an aberration corrected pattern $f_{corr}(2\theta)$ to reduce the effects of aberrations in representation of $f(2\theta)$, including performing the deconvolution point by point for different values of the parameter $2\theta$ using for each value of the parameter $2\theta$ a respective representation of the aberration function $F_{inst}$ for a respective value of the parameter $2\theta$.

The method can perform correction on the pattern over over a range of scattering angles incorporating multiple peaks rather than over the range of each peak separately. Preferably the method performs correction over more than half of the range, further preferably at least 80% of the range and most preferably substantially all of the range.

In this way, the aberration corrected X-ray diffraction pattern is obtained without requiring model information about the sample microstructure, or a model for peak positions, which means the corrected pattern, is much easier to obtain than in prior approaches incorporating aberrations corrections.

Moreover, the method is much more general than prior methods and has much broader scope of application, as it is nearly independent of the available information about the sample and equally applicable to nearly any type of aberration.

The aberrations corrected may in particular include instrumental aberrations, spectral and other effects.

The space may be a Fourier space and the representation of the aberration function $F_{inst}$ may be in particular a Fourier series, which may be for example be represented as complex numbers having modulus and complex argument.

The aberration corrected pattern $f_{corr}(2\theta)$ for a particular scattering angle $2\theta$ may be obtained by carrying out a modified inverse Fourier transform using the ratio obtained by dividing the values for for the measured pattern representation $F_{exp}$ by the respective value in the series representing the aberration $F_{inst}$ obtained for a similar scattering angle $2\theta$.

In an alternative embodiment the aberration corrected pattern $f_{corr}(2\theta)$ for a particular scattering angle $2\theta$ is obtained by carrying out a modified inverse Fourier transform using the $F_{exp}$ values multiplied by $\exp(-i\phi_{inst})$ factors, where $\phi_{inst}$ are the complex arguments of the Fourier coefficients $F_{inst}$ calculated for the similar particular values of $2\theta$.

This latter approach has the advantage that it is only uses the complex argument (phase) of the terms of the Fourier series representing the aberration. If the modulus is used as well, this can cause changes in the convergence of the Fourier series, which can lead to error and noise in the corrected series. The use of complex arguments allows the preservation of the original convergence rate of $F_{exp}$ that may be useful for subsequent analysis.

For the corrected pattern $f_{corr}(2\theta)$ it will results in resolution similar to $f(2\theta)$.

In embodiments of the invention additional background subtraction and regularization is applied to $F_{exp}$ to reduce numerical noise naturally present in the measured data. For the Fourier series regularization normally realized as extra suppression of high frequency Fourier coefficients by multiplication with regularization function.

The representation of the aberration functions may be obtained either by measuring some standard material or preferably by mathematical modelling. The latest approach is more general as being independent from the actual peak positions and quality of standard material.

In particular, the calculations may use the integral approach for mathematical modelling of aberrations proposed in Kogan and Kupryanov (1992) where summation over the different beam trajectories and spectral components directly delivers the aberration representation as Fourier series $F_{inst}$. This approach is thus ideally suited to the invention.

The non-monochromatic wavelength (energy) structure of the incoming radiation beam normally forms a multiple peak structure for any scattering instance. This makes interpretation of the pattern more difficult. In embodiments, the aberration correction method for an instrumental function is combined with with mathematical removal (deconvolution) of unwanted energy components.

The invention also relates to a measurement method including placing a sample in X-ray apparatus; measuring the X-ray pattern as a function of scattering angle to obtain the measured X-ray pattern, and correcting the measured pattern as set out above. The -X-ray apparatus may be for example diffractometer or small angle scattering camera or others delivering either X-ray diffraction pattern or small angle scattering pattern.

In another aspect of the invention there is provided a computer program product for carrying out the invention.

In a further aspect there is provided an apparatus comprising:

a source for emitting a beam;

a sample stage for mounting a sample;

a detector for measuring rays scattered from the sample to obtain a measured pattern $f(2\theta)$, as a function of a parameter $2\theta$ representing the scattering angle;

an output for outputting a corrected output scattering pattern as a function $2\theta$;

wherein the apparatus includes a correction device arranged:

i) to calculate the representation of the measured pattern $f(2\theta)$ in a space for applying such corrections;

ii) to obtain a representation of an aberration function including a description of instrumental aberrations $F_{inst}$ depending on the parameter $2\theta$ in the same space; and iii) to perform deconvolution of the calculated representation of $f(2\theta)$ to create an aberration corrected pattern $f_{corr}(2\theta)$ to reduce the effects of aberrations in representation of $f(2\theta)$, including performing the deconvolution point by point for different values of the parameter $2\theta$ using for each value of the parameter $2\theta$ a respective representation of the aberration function $F_{inst}$ for a respective value of the parameter $2\theta$.

The apparatus may output automatically a corrected diffraction pattern normalised to correct for abberations. This may be done with no user intervention. The corrected diffraction pattern is much easier to use as a basis for processing.

BRIEF DESCRIPTION OF DRAWINGS

For a better understanding of the invention, an embodiment will now be described with reference to FIGS. 1 to 5 in which.

DETAILED DESCRIPTION

Figure 1:
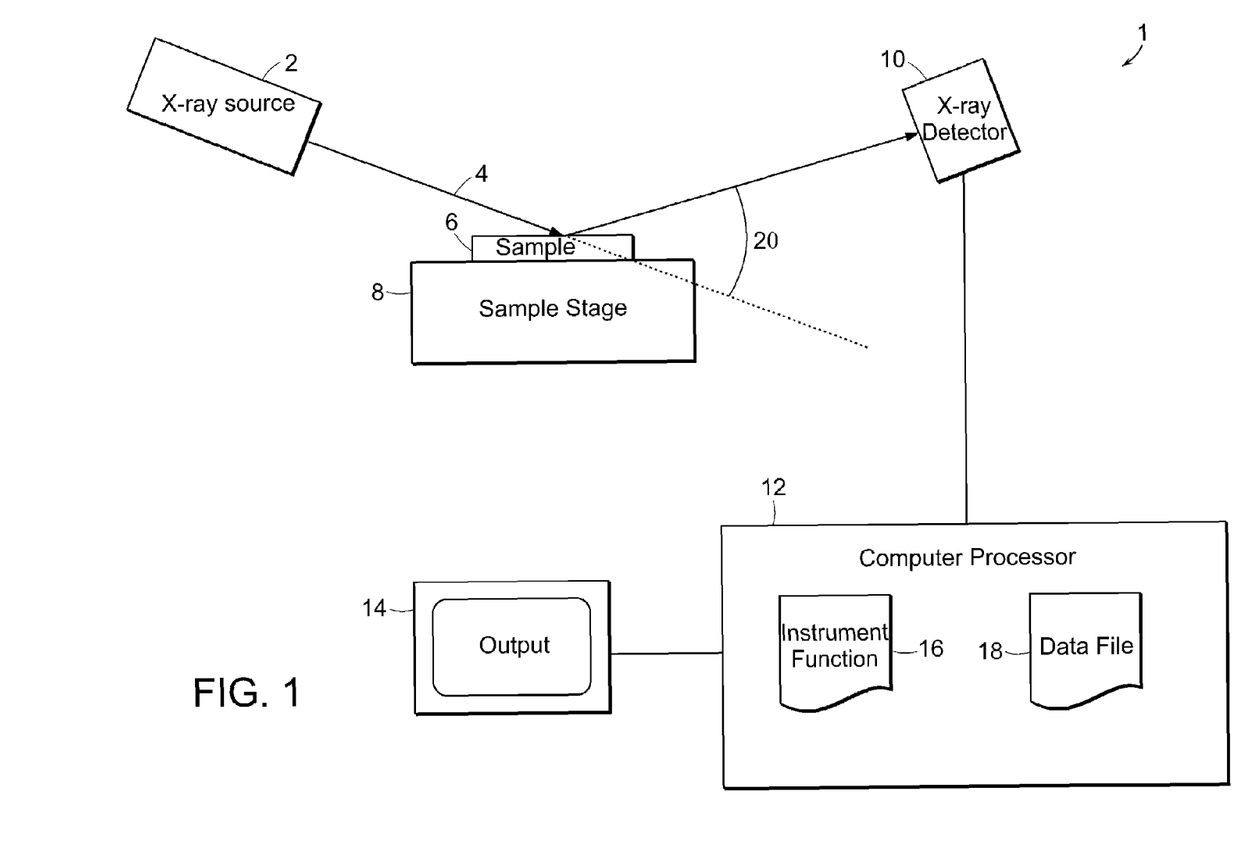
FIG. 1 shows apparatus in accordance with an embodiment of the invention.

FIG. 1 shows a schematic X-ray diffraction apparatus 1 according to an embodiment of the invention.

An X-ray source 2 is arranged to supply a beam of X-rays 4 onto sample 6 on sample stage 8. The X-rays are diffracted and measured by X-ray detector 10 as a function of scattering angle 2θ.

The skilled person will be aware of a variety of different arrangements that can be used to vary the angle, for example by mounting the source 2 and detector 10 on separate goniometers, and varying the angle. Further, additional monochromators or crystals may be used to improve resolution and accuracy.

The measured scattered X-ray intensity as a function of 2θ is output to internal computer processor 12, which is arranged to carry out correction (cleaning) of the data and to output the cleaned data on output 14, which may be a computer interface, screen, printer, or any suitable output device as will be appreciated by those skilled in the art.

The computer processor 12 is programmed with code arranged to cause the processor 12 to carry out the method of correcting (cleaning) the data for aberrations which will now be described and explained in more detail.

The measured and optionally background corrected pattern may be considered as being made up of a number of components, each component normally being a peak. These components will be indexed by variable j, and will have Bragg position $2\theta_j$ and total weight $A_j$. Each peak will have a shape function $f_0(2\theta-2\theta_j, 2\theta_j)$, normalised to 1, so that the k total peak shape is given by $A_j f_0(2\theta-2\theta_j, 2\theta_j)$ as a function of 2θ.

Thus, the total intensity as a function of 2θ from a superposition of a number of separate peaks is given by:

$$I_{calc}(2\theta) = \sum_j A_j f_0(2\theta - 2\theta_j, 2\theta_j). \tag{1}$$

The same equation in the Fourier space is:

$$F_{calc}(H) = \sum_j A_j F_0(H, 2\theta_j) \exp\left(\frac{2\pi i H}{T} 2\theta_j\right) \tag{2}$$

where H is the number of the Fourier coefficient, T is the complete angular interval over which the pattern is transformed, and i is the square root of (−1).

A single peak is considered to be the convolution of instrumental, physical and spectral parts in real space, and so in Fourier space the peak $F_0(H, 2\theta_j)$ is the product of the instrumental Fourier coefficient $F_{inst}(H,2\theta_j)$, the physical part $F_{phys}(H,2\theta_j)$, and the spectral part $F_{Spec}(H,2\theta_j)$. The spectral part relates to the effect of a non totally monochromatic spectrum, the instrumental coefficient relates to the instrumental arrangement in particular non-ideally narrow collimators and detectors and the physical part relates to the effects related to the sample nature for example small size crystallites.

The instrumental coefficients $F_{inst}(H,2\theta_j)$ may be obtained directly by calculation using the method of [Kogan et al, 1992] set out above.

The main asymmetry in the single peak is mainly associated with the instrumental coefficients $F_{inst}(H,2\theta_j)$. However, a similar formalism as described below may be used when the effects of peak asymmetry are associated with the physical or spectral factors.

Since multiplication in Fourier space is the equivalent of convolution in real space, equation (2) may be represented as:

$$F_{calc}(H) = \sum_j A_j F_{inst}(H, 2\theta_j) F_{phys}(H, 2\theta_j) F_{spec}(H, 2\theta_j) \exp\left(\frac{2\pi i H}{T} 2\theta_j\right) \tag{3}$$

Due to the dependence on 2θ, deconvolution of the functions $F_{inst}$, $F_{phys}$, $F_{spec}$ in (3) from a measured pattern with more than one peak is essentially impossible.

In the present case, in general the shape of a single peak, given by the single peak function $f_0(2\theta-2\theta_j, 2\theta_j)$ is asymmetric. This means that the Fourier transform of the single peak has coefficients $F_0(H, 2\theta_j)$ that are complex numbers with both nonzero real and imaginary part.

It is convenient to use the modulus-argument form of such numbers, representing the complex number as the product of the complex modulus and exponent of the complex argument of the complex number, where the modulus $M_0(H)$ determines convergence rate and complex argument $\phi_0(H)$ determines the asymmetry of the peak. If $\phi_0(H)=0$ for all H this would mean a symmetrical peak function.

$$F_0(H) = M_0(H)\exp(i\varphi_0(H)) \tag{4}$$

$$\varphi_0(H) = \arctan\left(\frac{\text{Im}(F_0(H))}{\text{Re}(F_0(H))}\right) \tag{5}$$

$$M_0(H) = \sqrt{|(F_0(H))|^2} \tag{6}$$

The present embodiment is concerned with a way of removing the effect of an instrumental function $F_{inst}$ causing asymmetry and peak shifts from measured data. This will be referred to as "cleaning".

The simplest version of "cleaning" correction in the case that there is only a single peak is based on the replacement of actual Fourier coefficients by the modulus of the Fourier coefficients. This therefore replaces the actual profile functions by symmetrical profile functions having a similar convergence of the original Fourier spectrum.

$$F_0'(H)=M_0(H) \text{ or } F_0'(H)=F_0(H)\exp(-i\phi_0(H)) \tag{7}$$

In general however, there is more than one peak.

In the first case (case 1), assume that each peak exibits a similar instrumental function.

In this case, a "cleaning" transform similar to (7) being applied to experimental Fourier coefficients $F_{exp}(H)$ will directly deliver corrected Fourier coefficients $F_{exp}'(H)$ (8):

$$F_{exp}'(H)=F_{exp}(H)\exp(-i\phi_{inst}(H)) \qquad (8)$$

The coefficients $F'_{exp}(H)$ therefore will represent a superposition of peaks with symmetrical shape in the real space. This transform is less prone to numerical errors than traditional deconvolution $$F_{exp}''(H)=F_{exp}(H)/F_{inst}(H) \qquad (9)$$

because the convergence rate of $F_{exp}'(H)$ stays unchanged using equation (8), unlike equation (9).

Generally traditional deconvolution approach (9) is also applicable for case 1 combined with subsequent regularization.

In practice, this situation with a like instrument function for each peak is not realistic except perhaps when the pattern is measured over the small range of 2θ angles.

Therefore, in general (case 2) $\phi_{inst}(H)$ should be considered as 2θ dependent: $\phi_{inst}(H,2\theta)$.

In these practically realistic cases when the complex argument $\phi_{inst}(H,2\theta)$ is 2θ dependent, equations (8) or (9) normally cannot be used.

The "cleaning" procedure according to this embodiment is designed to overcome this problem by some physically realistic approximations.

The first approximation is to consider $\phi_{inst}(H,2\theta)$ as being a smooth, slowly changing function of 2θ. As a result, it may be assumed that $\phi_{inst}(H,2\theta)$ is constant over the typical angular range of the single peak definition, say a 1°-3° variation in 2θ.

If we now fix 2θ as a parameter at certain 2ψ value, and apply transform (10) similar to (8), with $\phi_{inst}(H,2\Psi)$ calculated for particular 2ψ, we will obtain corrected "Fourier coefficients" $F'_{exp}(H,2\Psi)$ being "correct" for the particular 2ψ value, corrected for asymmetry:

$$F'_{exp}(H,2\Psi)=F_{exp}(H)\exp(-i\phi_{inst}(H,2\Psi)) \qquad (10)$$

It means that if we use $F'_{exp}(H,2\Psi)$ for the inverse Fourier transform over complete range of 2θ:

$$I'_{exp}(2\theta, 2\Psi) = \sum_H F'_{exp}(H, 2\Psi)\exp\left(-\frac{2\pi iH}{T}2\theta\right) \qquad (11)$$

we may expect to obtain the pattern $I'_{exp}(2\theta, 2\psi)$ with the correct asymmetry removal for the peaks close to 2ψ value and otherwise less correct asymmetry removal far away from 2ψ.

Note that transform (11) is similar to transform (8) in the vicinity of 2ψ and therefore will not affect the integral weights $A_j$ for the components in the vicinity of 2ψ.

The final step of the "cleaning" procedure is based on the calculation of intensity in each point $I'_{exp}(2\theta, 2\psi)$ by the transform (11) with coefficients $F'_{exp}(H,2\Psi)$ taken at 2ψ=2θ:

$$I'_{exp}(2\theta) = \sum_H F'_{exp}(H, 2\theta)\exp\left(-\frac{2\pi iH}{T}2\theta\right) \qquad (12)$$

The assumption made here is that experimental Fourier coefficients corrected for the complex argument shift in particular point 2θ may be used for the synthesis of the corrected pattern in this particular point.

Rewriting (12) with (10) we obtain an equation for the corrected, "cleaned" pattern:

$$I'_{exp}(2\theta) = \sum_H F_{exp}(H)\exp(-i\varphi_{inst}(H, 2\theta))\exp\left(-\frac{2\pi iH}{T}2\theta\right) \qquad (13)$$

where $\phi_{inst}(H,2\theta)$ may be obtained theoretically by method mentioned above [Kogan et al 1992].

Alternatively, $\phi_{inst}(H,2\theta)$ may be determined experimentally by measuring standard samples for which the theoretical pattern is known.

Figure 2:
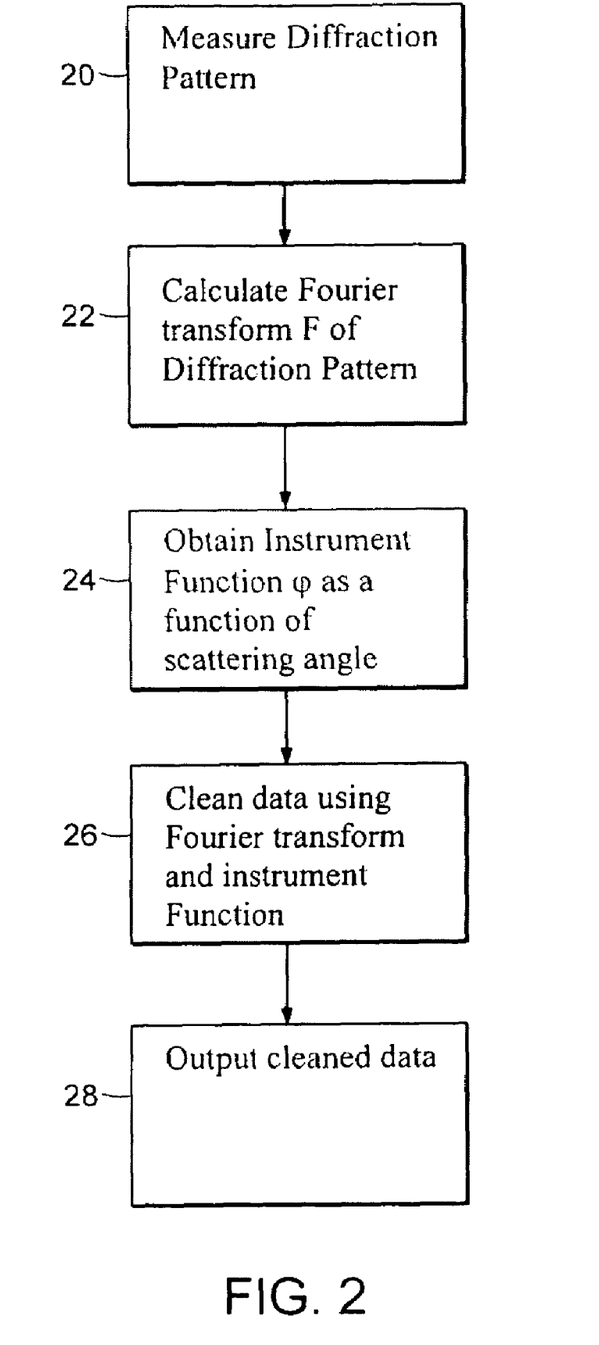
FIG. 2 shows a flow diagram of a method in accordance with the invention.

Thus, referring to FIG. 2, in use a sample is placed in the apparatus and a measured pattern obtained (step 20) with a plurality of peaks. However, note that the method does not require these peaks to be identified, or fitted or described. It means that the measured pattern may be processed as a single continuum without investigation of its internal structure.

Next, the Fourier transform F of the measured data is obtained (step 22), in the embodiment using a Fast Fourier Transform algorithm for simplicity although other algorithms may be used if required.

The instrument function $\phi_{inst}(H,2\theta)$ is obtained, from storage (step 24). This function may conveniently be stored in the computer processor 12 of the particular instrument 1. The store may be in the form of a table of values or any other convenient representation of the function.

Then, equation (13) is applied to transform the data (step 26) with the known $\phi_{inst}(H,2\theta)$ function 16.

This gives a corrected output of measured intensity as a function of scattering angle 2θ, which is output (step 28). The output function may alternatively or additionally be stored as a data file 18 to allow ready comparison with other data.

Thus, the instrument gives an output corrected for the aberration without any need for operator intervention, information about the peaks, or assumptions about the type of sample. The correction is therefore much simpler to implement than prior art approaches, which may require an exact model of the crystalline unit cell, or atomic structure.

Indeed, the user can simply treat the whole apparatus 1 as a black box outputting corrected measured intensity as a function of scattering angle. This has not previously been possible, because previous correction approaches required additional user input.

Thus, the apparatus allows corrected spectra to be measured even in environments where skilled personnel are not present to supply suitable inputs to correct the spectra.

The apparatus is also much simpler to use, and this is of course of value even when skilled personnel are present.

At present, because of the difficulty of carrying out corrections, in practice measured data are stored and compared. However, such measured data includes the aberrations caused by the instrument function and accordingly is not readily comparable between equipment or even when measured using different optics on the same equipment. This is particularly the case for samples having peaks measured at low angles such as pharmaceutical and nano-material samples.

The invention allows ready comparison between these samples and measurements that is important for example to realise search-match in the database with reference patterns.

The invention is not limited to the correction of the influence of instrumental functions but may also incorporates the elimination of effects from unwanted radiation components, including for example Cu Kα2, Kα3, Kβ, Lα lines. In this case, equation (13) may be changed to:

$$I'_{\exp}(2\theta) = \sum_H F_{\exp}(H)F_{sc}(H, 2\theta)\exp(-i\varphi_{inst}(H, 2\theta))\exp\left(-\frac{2\pi iH}{T}2\theta\right) \quad (14)$$

where $$F_{sc}(H, 2\theta) = \frac{A_p F_p(H, 2\theta_p)}{\sum_k A_k F_k(H, 2\theta_k)\exp\left(\frac{2\pi iH}{T}(2\theta_k - 2\theta_p)\right)} \quad (15)$$

with index p indicating the main spectral component and index k listing both main and unwanted components that should be removed.

For example, to remove the effects of the Cu Kα1 and Kα2 doublet, where the Kα1 is the dominant peak, $F_p$ is the fourier transform of the Kα1 line shape and $F_k$ is the Fourier transform of the Kα1 line shape for k=1 and the Kα2 line shape for k=2. In this simple case, k only runs to two peaks but in general k can reflect many different components of the spectrum used to take the measurement.

The invention may be used to convert from a complex peak shape to a known analytical function, such as for example Gauss, Lorenzian, or Voight.

The invention allows the conversion of measured data to results as if the results would be measured on other device. The conversion may be applied before or after carrying out analytical techniques in an analytical package. After the "cleaning" is applied and asymmetry removed, the pattern may be analysed in an easier fashion using simpler analytical models. For example, the pattern from the reference material obtained on one device converted to user device for use in search-match procedure or quantitative phase analysis.

In many cases the "cleaning" procedure may be applied without prior background correction of measured pattern. The procedure seems to be nearly non-sensitive to the background.

The corrected patterns may be stored in a database 18 as device-and-optics independent information The diffractometer may deliver "cleaned" patterns as an output for the user.

Figure 3:
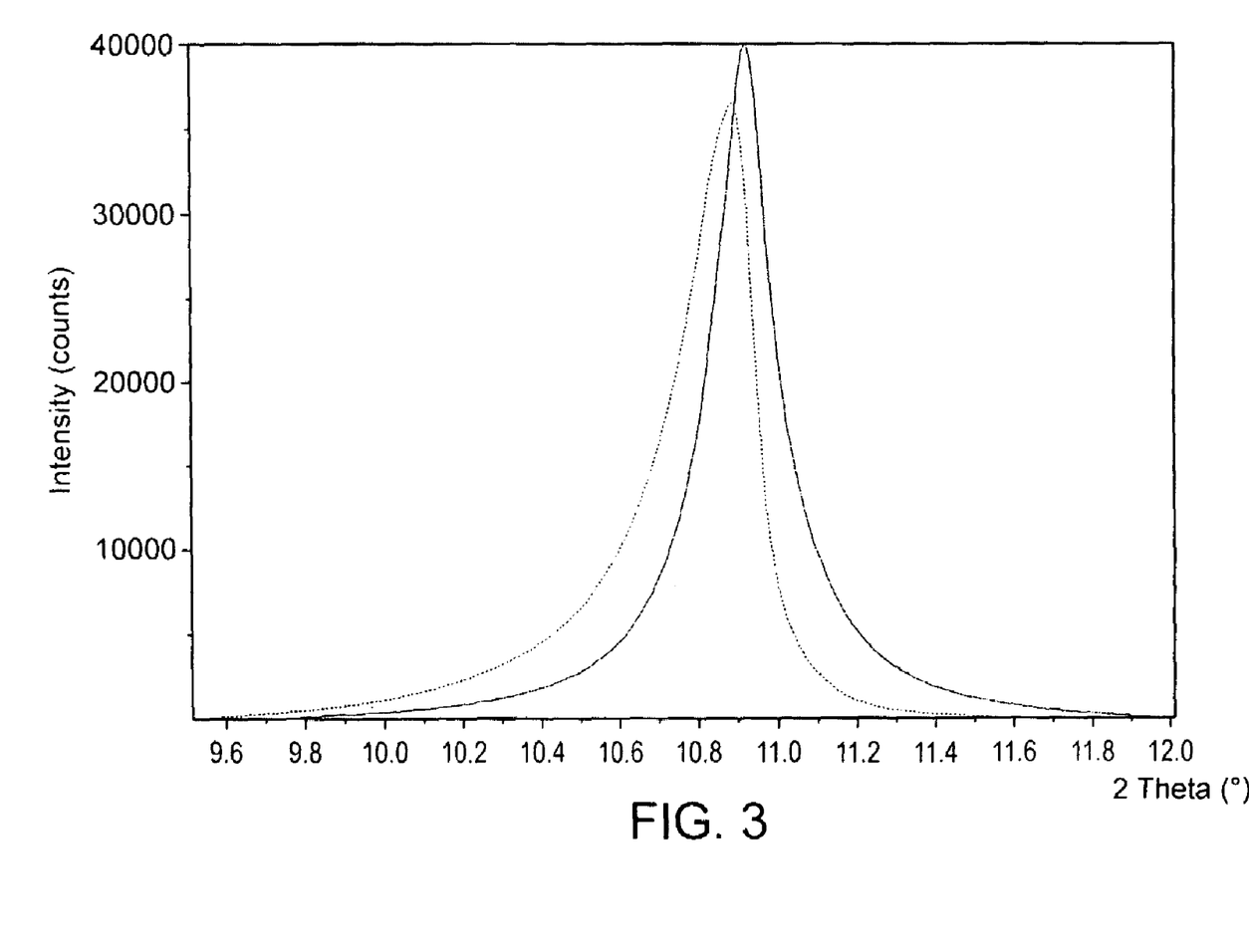
FIG. 3 shows a first example of cleaning a spectrum using a method according to the embodiment.

FIG. 3 shows a single simulated peak as a dotted line at low 2θ which is a convolution of instrumental, spectral and physical functions.

The same peak corrected according to equation 13 is shown as a full line. Note that the asymmetry and the shift from the true (Bragg) peak position have been corrected.

Figure 4:
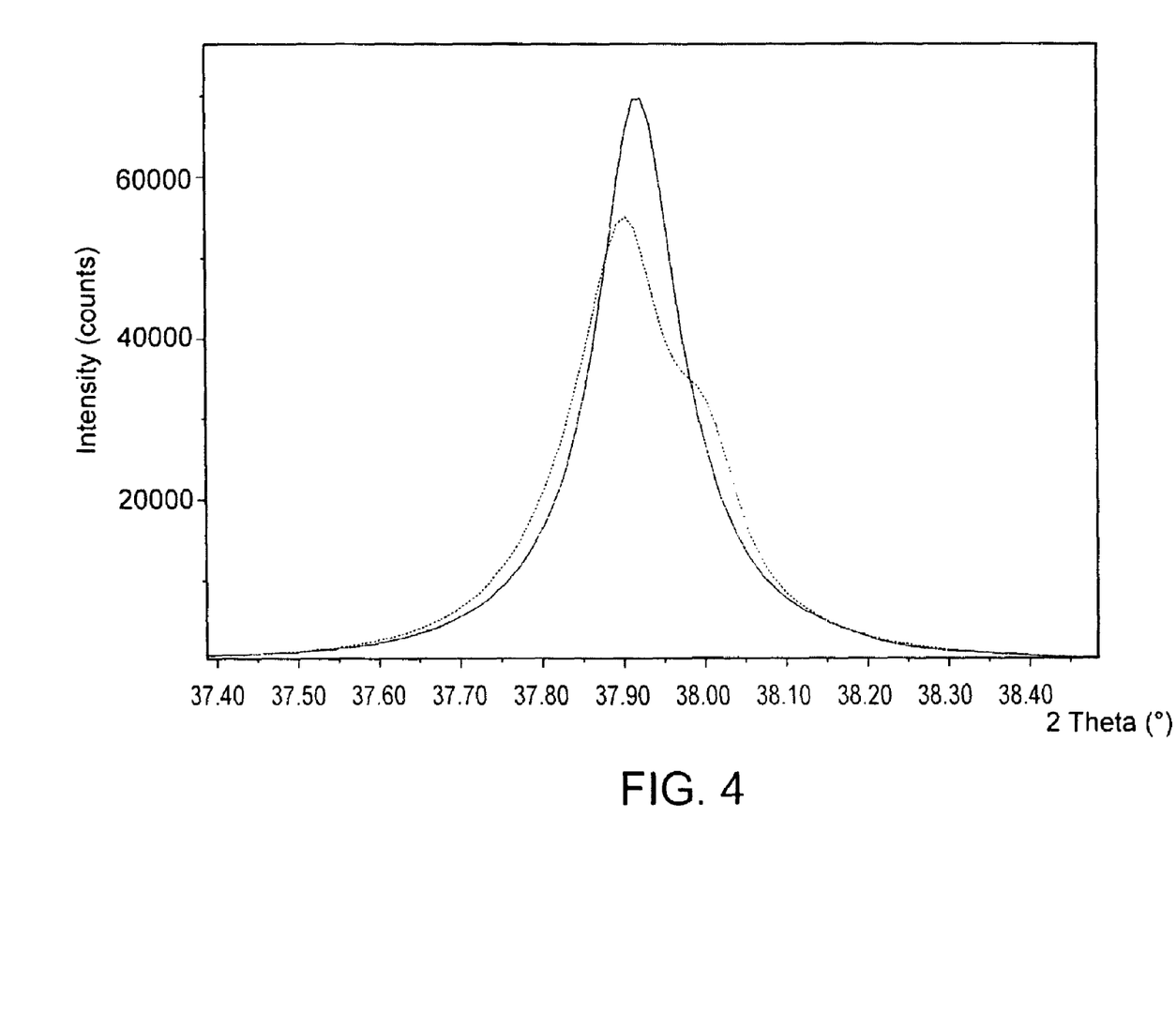
FIG. 4 shows a second example of cleaning a spectrum using a method according to the embodiment.

FIG. 4 shows a further single peak as a dotted line measured using a source with both Kα1 and Kα2 lines. The double spectral line used to take the measurement results in a double peak even though the diffraction peak is in fact a single peak. The full line shows the peak after a cleaning algorithm is applied to remove both the effect of peaks asymmetry and the effect of the Kα2 line using equation 14. Note that not merely is asymmetry removed but also the second (Kα2) component.

Figure 5:
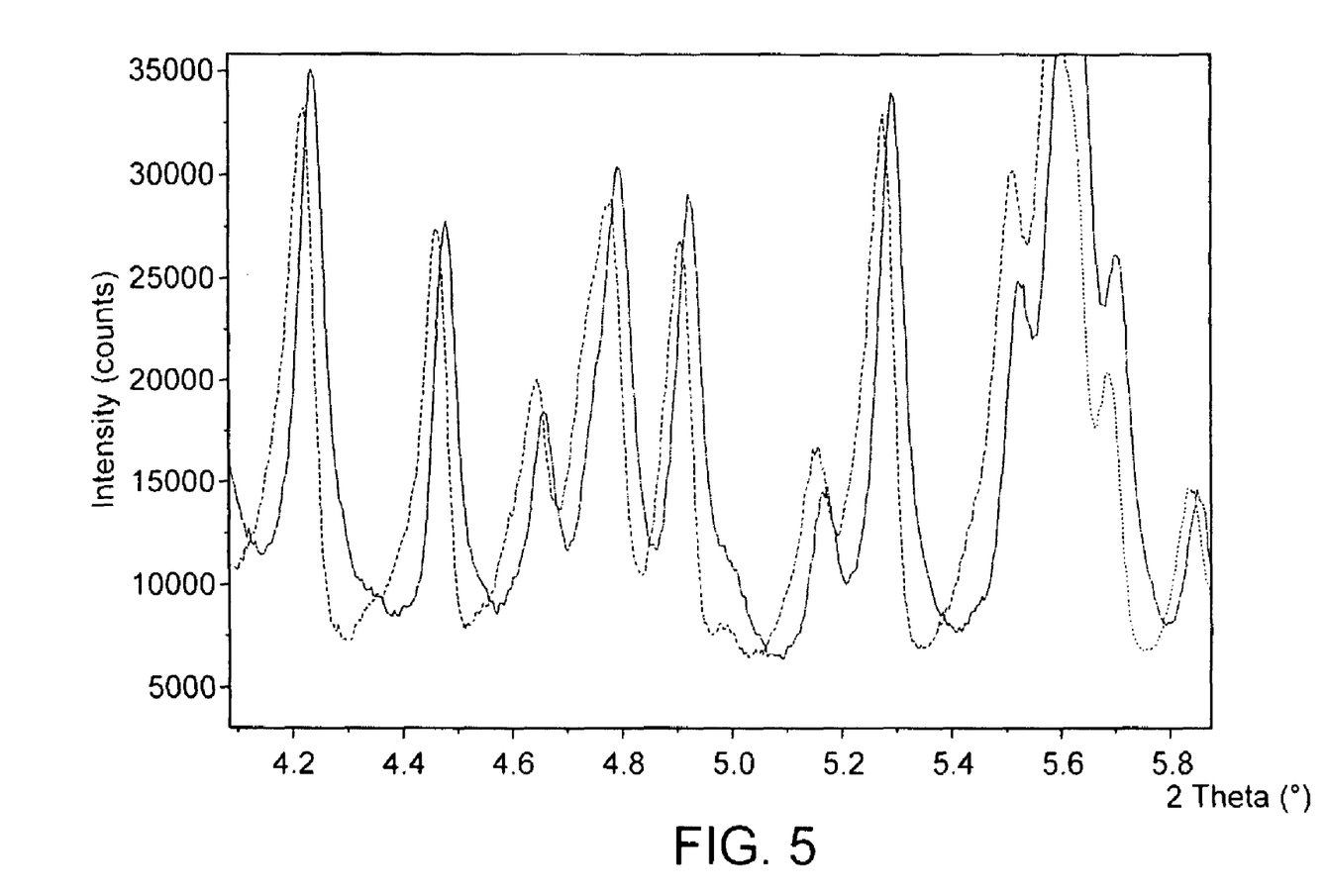
FIG. 5 shows a third example of cleaning a spectrum using a method according to the embodiment.

The invention is of particular benefit with multiple peak structures such as the diffraction pattern of a complex protein structure (in the example lysozome) shown in FIG. 5. Again, the dotted line shows the uncleaned data and the solid line the cleaned data. Again, much better peak symmetry and correct peak position is obtained without any reference to the model of protein structure or to model of peaks.

The invention is not limited to the examples discussed above and variations are possible.

In particular, although the invention is described to correct for the instrument function or spectral function it may used to correct for any other effect or aberration.

Although the above description relates to X-rays the same approach may be used with electron or neutron scattering, spectroscopy, both X-ray and optical, nuclear magnetic resonance (NMR), EXAFS.

The beam need not be from an X-ray tube but may be for example from a synchrotron.

Although the above description uses the scattering angle as the measure of the amount of scattering other measures may be used, including the energy or a measure of scattering such as for example displacement of the detector which is related to scattering angle.

What is claimed is:

1. A method for correcting a measured scattering pattern containing multiple significantly distant components and/or peaks for the effects of aberration influencing the component and/or peak shapes and/or positions, the method including:
   i) inputting a measured pattern f(2θ) as a function of a parameter 2θ representing the scattering angle, and calculating a representation of the measured pattern f(2θ) in a space for applying corrections;
   ii) obtaining a representation of an aberration function including a description of instrumental aberrations $F_{inst}$ depending on the parameter 2θ in the same space; and
   iii) performing deconvolution of the calculated representation of f(2θ) to create an aberration corrected pattern $f_{corr}(2\theta)$ to reduce the effects of aberrations in representation of f(2θ), including performing the deconvolution point by point for different values of the parameter 2θ using for each value of the parameter 2θ a respective representation of the aberration function $F_{inst}$ for a respective value of the parameter 2θ.

2. The method according to claim 1 wherein:
   the space for applying corrections is Fourier space;
   the representation of the measured pattern f(2θ) is a fourier series $F_{exp}$; and
   the representation of the aberration function $F_{inst}$ is a Fourier series, the coefficients of the aberration function being a function of the parameter 2 θ.

3. The method according to claim 2 wherein the deconvolution to obtain the aberration corrected pattern $f_{corr}(2\theta)$ for a particular value of the parameter 2θ is obtained by carrying out a modified inverse Fourier transform using the ratio obtained by dividing the $F_{exp}$ values by the respective values representing the aberration $F_{inst}$ obtained for the similar particular values of the parameter 2θ.

4. The method according to claim 2 wherein the deconvolution to obtain the aberration corrected pattern $f_{corr}(2\theta)$ for a particular value of the parameter 2θ is obtained by carrying out a modified inverse Fourier transform using the $F_{exp}$ values multiplied by $\exp(-i\Phi_{inst})$ factors, where $\Phi_{inst}$ are the complex arguments of the Fourier coefficients $F_{inst}$ calculated for the similar particular values of the parameter 2θ.

5. The method depending on claim 3 where additional regularization or noise filtering or background subtraction is applied to $F_{exp}$ for carrying out the modified inverse Fourier transform.

6. The method according to claim 2 including obtaining the Fourier series representing the aberration $F_{inst}$ as a function of the parameter 2θ using measurements on reference materials.

7. The method according to claim 2 including obtaining the Fourier series representing the aberration $F_{inst}$ as functions of the parameter 2θ based on mathematical modelling of aberrations.

8. The method according to claim 7 including summing over the possible values of parameters influencing aberration, for example beam trajectories or energy spectrum in the measuring instrument to obtain the mathematical model of aberration.

9. The method according to claim 7 including summing over the possible values of parameters influencing aberration performed directly to sum the inputs to $F_{inst}$ values.

10. The method according to claim 2 where point by point Fourier deconvolution of the Fourier series $F_{exp}$ from the aberration representation $F_{inst}$ for the particular parameter $2\theta$ is combined with deconvolution of multiple energy components structure modelled for the particular parameter $2\theta$ range while multiple components structure associated with particular scattering instance say the single system of crystallographic planes.

11. The method according to preceding claim 1 further comprising placing a sample in X-ray apparatus; and measuring the X-ray pattern as a function of scattering angle or energy to obtain the measured pattern $f(2\theta)$.

12. The method according to claim 1, comprising inputting measured pattern for a plurality of samples; calculating the aberration corrected pattern as a function of scattering angle or energy for each of the samples, and storing and/or analysing the aberration corrected patterns.

13. A method for pattern comparison or analysis, the method including:
  correcting measured data using:
    i) inputting a measured pattern $f(2\theta)$ as a function of a parameter $2\theta$ representing the scattering angle, and calculating a representation of the measured pattern $f(2\theta)$ in a space for applying corrections;
    ii) obtaining a representation of an aberration function including a description of instrumental aberrations $F_{inst}$ depending on the parameter $2\theta$ in the same space; and
    iii) performing deconvolution of the calculated representation of $f(2\theta)$ to create an aberration corrected pattern $f_{corr}(2\theta)$ to reduce the effects of aberrations in representation of $f(2\theta)$, including performing the deconvolution point by point for different values of the parameter $2\theta$ using for each value of the parameter $2\theta$ a respective representation of the aberration function $F_{inst}$ for a respective value of the parameter $2\theta$, and using a convolution based method to simulate similarity of devices used for the measurements.

14. A method for pattern comparison including correcting measured data using:
  i) inputting a measured pattern $f(2\theta)$ as a function of a parameter $2\theta$ representing the scattering angle, and calculating a representation of the measured pattern $f(2\theta)$ in a space for applying corrections;
  ii) obtaining a representation of an aberration function including a description of instrumental aberrations $F_{inst}$ depending on the parameter $2\theta$ in the same space; and
  iii) performing deconvolution of the calculated representation of $f(2\theta)$ to create an aberration corrected pattern $f_{corr}(2\theta)$ to reduce the effects of aberrations in representation of $f(2\theta)$, including performing the deconvolution point by point for different values of the parameter $2\theta$ using for each value of the parameter $2\theta$ a respective representation of the aberration function $F_{inst}$ for a respective value of the parameter $2\theta$,
  and a convolution based method to simulate similarity of samples properties as density or sample layout.

15. A computer program product comprising a computer readable medium having computer executable program code thereon, the computer executable program code comprising:
  i) program code for inputting a measured pattern $f(2\theta)$ as a function of a parameter $2\theta$ representing the scattering angle, and calculating a representation of the measured pattern $f(2\theta)$ in a space for applying corrections;
  ii) program code for obtaining a representation of an aberration function including a description of instrumental aberrations $F_{inst}$ depending on the parameter $2\theta$ in the same space; and
  iii) program code for performing deconvolution of the calculated representation of $f(2\theta)$ to create an aberration corrected pattern $f_{corr}(2\theta)$ to reduce the effects of aberrations in representation of $f(2\theta)$, including performing the deconvolution point by point for different values of the parameter $2\theta$ using for each value of the parameter $2\theta$ a respective representation of the aberration function $F_{inst}$ for a respective value of the parameter $2\theta$.

16. An apparatus comprising:
  a source for emitting a beam;
  a sample stage for mounting a sample;
  a detector for measuring rays scattered from the sample to obtain a measured pattern $f(2\theta)$, as a function of a parameter $2\theta$ representing the scattering angle; an output for outputting a corrected output scattering pattern as a function $2\theta$; wherein the apparatus includes a correction device arranged:
    i) to calculate a representation of the measured pattern $f(2\theta)$ in a space for applying corrections;
    ii) to obtain a representation of an aberration function including a description of instrumental aberrations $F_{inst}$ depending on the parameter $2\theta$ in the same space; and
    iii) to perform deconvolution of the calculated representation of $f(2\theta)$ to create an aberration corrected pattern $f_{corr}(2\theta)$ to reduce the effects of aberrations in representation of $f(2\theta)$, including performing the deconvolution point by point for different values of the parameter $2\theta$ using for each value of the parameter $2\theta$ a respective representation of the aberration function $F_{isnt}$ for a respective value of the parameter $2\theta$.

17. The apparatus according to claim 16 where the representation $F_{isnt}$ is a Fourier series and the correction device is arranged to calculate the aberration corrected pattern by modified inverse Fourier transform using the ratio obtained by dividing the representation $F_{exp}$ by the respective value in the series representing the aberration $F_{isnt}$ for the particular scattering angle $2\theta$.

18. The apparatus according to claim 16 wherein where the series $F_{isnt}$ is a Fourier series and the correction device is arranged to calculate the corrected output pattern by carrying out a modified inverse Fourier transform using the $F_{exp}$ values multiplied by $exp(-i\Phi_{inst})$ factors, where $\Phi_{isnt}$ are the complex arguments of the Fourier coefficients $F_{isnt}$ calculated for the similar particular values of $2\theta$.

19. The apparatus according to claim 16 wherein the representation $F_{isnt}$ is predetermined and stored in the correction device.

20. The apparatus according to claim 16 wherein the apparatus is X-ray scattering apparatus or x-ray diffraction apparatus, the source being an X-ray source and the detector being an X-ray detector.

21. The apparatus according to claim 16 wherein the apparatus uses the correction device to automatically deliver the corrected output scattering pattern having reduced aberration as the output.

22. The apparatus according to claim 21 further comprising a computer arranged to process the output scattering pattern having reduced aberration and to carry out subsequent data analysis including at least one of: indexing the unit cell; fitting the output scattering pattern to at least one scattering profile; phase analysis; line profile analysis; structure refinement; structure determination; stress and texture analysis, and a method of analysis of small angle scattering data.

23. An apparatus comprising:
   i) a database containing scattering patterns corrected by a method including the steps of:
      i) inputting a measured pattern $f(2\theta)$ as a function of a parameter $2\theta$ representing the scattering angle, and calculating a representation of the measured pattern $f(2\theta)$ in a space for applying corrections;
      ii) obtaining a representation of an aberration function including a description of instrumental aberrations $F_{isnt}$ depending on the parameter $2\theta$ in the same space; and
      iii) performing deconvolution of the calculated representation of $f(2\theta)$ to create an aberration corrected pattern $f_{corr}(2\theta)$ to reduce the effects of aberrations in representation of $f(2\theta)$, including performing the deconvolution point by point for different values of the parameter $2\theta$ using for each value of the parameter $2\theta$ a respective representation of the aberration function $F_{isnt}$ for a respective value of the parameter $2\theta$, and
   ii) analyzing means for analyzing the data from the database including at least one of carrying out arithmetic operations, comparison, search-match analysis, and cluster analysis.

* * * * *